(12) United States Patent
Maehara et al.

(10) Patent No.: US 6,344,572 B1
(45) Date of Patent: Feb. 5, 2002

(54) PROCESSES FOR THE PREPARATION OF THREO-1,2-EPOXY-3-AMINO-4-PHENYLBUTANE DERIVATIVES

(75) Inventors: Katsuji Maehara, Kobe; Yukinori Tokuda, Kakogawa; Hiroshi Murao, Takasago; Yasuyoshi Ueda, Himeji, all of (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 09/647,340

(22) PCT Filed: Jan. 31, 2000

(86) PCT No.: PCT/JP00/00495
§ 371 Date: Nov. 17, 2000
§ 102(e) Date: Nov. 17, 2000

(87) PCT Pub. No.: WO00/44736
PCT Pub. Date: Aug. 3, 2000

(30) Foreign Application Priority Data

Jan. 29, 1999 (JP) ............................................. 11-021640
Aug. 26, 1999 (JP) ............................................. 11-239720

(51) Int. Cl.⁷ ............................................... C07D 301/02
(52) U.S. Cl. ....................................... 549/514; 549/513
(58) Field of Search ................................... 549/513, 514

(56) References Cited

U.S. PATENT DOCUMENTS 5,481,011 A * 1/1996 Chen et al. .................. 549/514

\* cited by examiner

*Primary Examiner*—Zinna Northington Davis
(74) *Attorney, Agent, or Firm*—Connolly Bove Lodge & Hutz

(57) ABSTRACT

The present invention provides a production method of high quality threo-1,2-epoxy-3-amino-4-phenylbutane derivatives (1) on a commercial scale in a simple, easy and efficient manner and with very high productivity, which comprises treating a threo-1-halo-2-hydroxy-3-amino-4-phenylbutane derivative (2) with a base in a polar organic solvent or a solvent composed of a polar organic solvent and water, and adding the resulting reaction mixture to water to thereby cause the resulting threo-1,2-epoxy-3-amino-4-phenylbutane derivative (1) to crystallize out.

42 Claims, 1 Drawing Sheet

PROCESSES FOR THE PREPARATION OF THREO-1,2-EPOXY-3-AMINO-4-PHENYLBUTANE DERIVATIVES

"This application is a 371 application of PCT/JP00/00495 filed Jan. 31, 2000."

TECHNICAL FIELD

The present invention relates to a production method of a threo-1,2-epoxy-3-amino-4-phenylbutane derivative represented by the following general formula (1):

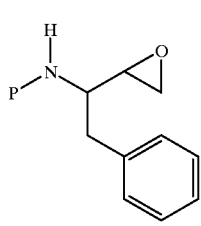

(1)

wherein P represents a urethane-type amino-protecting group and the configurations at 2 and 3 positions are (2S,3R) or (2R,3S). The threo-1,2-epoxy-3-amino-4-phenylbutane derivatives (1), in particular (2R,3S)-1,2-epoxy-3-amino-4-phenylbutane derivatives, are compounds useful as intermediates for the production of various HIV proteases, as described in Japanese Kokai Publication Hei-05-230095.

BACKGROUND ART

The hitherto-known production technology for threo-1,2-epoxy-3-amino-4-phenylbutane derivatives (1), in particular (2R,3S)-1,2-epoxy-3-amino-4-phenylbutane derivatives, includes a method which comprises synthesizing (2R,3S)-1,2-epoxy-3-N-(tert-butoxycarbonyl)amino-4-phenylbutane by epoxidizing 2(S)-N-(tert-butoxycarbonyl)amino-1-phenyl-3-butene with m-chloroperbenzoic acid in methylene chloride (e.g. J. Org. Chem., 1987, vol. 52, page 1487; Japanese Kokai Publication Hei-05-230095). Further, there is also known the method for isolating (2R,3S)-1,2-epoxy-3-amino-4-phenylbutane derivatives, which comprises carrying out ether extraction and washing repeatedly, drying the organic phase over anhydrous sodium sulfate, evaporating the solvent, purifying the residue by silica gel column chromatography (eluent: hexane/ethyl acetate=4/1) and recrystallizing the product from hexane (Japanese Kokai Publication Hei-05-230095).

However, the prior art methods pose serious problems in carrying out them on an industrial scale; for example, the reaction yield of (2R,3S)-1,2-epoxy-3-N-(tert-butoxycarbonyl)amino-4-phenylbutane is low, namely about 80 mole percent (J. Org. Chem., 1987, vol. 52, page 1487); it is necessary to use undesirable reagents (e.g. methylene chloride, which is a halogenated hydrocarbon, ether and hexane, which are very inflammable organic solvents, and m-chloroperbenzoic acid, which is a very hazardous peroxide, or the like) ; a plurality of organic solvents are used in large quantities; the procedure is complicated; and the productivity is low.

In the prior art methods, silica gel column chromatography (eluent: hexane/ethyl acetate=4/1) and/or recrystallization from hexane is carried out for purification and isolation of (2R,3S)-1,2-epoxy-3-N-(tert-butoxycarbonyl)amino-4-phenylbutane. Such an isolation procedure, however, involves serious problems in carrying it out on a commercial scale; for example, use of large amounts of undesirable reagents, complexity of the process, a waste of time resulting from the complicatedness, increases in the number and capacity of production units, and low yields. A further problem is that the product crystallized from hexane has a low density, hence a large capacity container is required for packaging crystals of the above compound.

In particular, investigations made by the present inventors revealed that the affinity of (2R,3S)-1,2-epoxy-3-N-(tert-butoxycarbonyl)amino-4-phenylbutane and other threo-1,2-epoxy-3-amino-4-phenylbutane derivatives (1) with various organic solvents is not suitable, which makes it very difficult to isolate high-quality crystals in good yield by crystallization at an appropriate crystallization concentration.

Thus, there is no effective method available in the art for producing a threo-1,2-epoxy-3-amino-4-phenylbutane derivative (1), in particular (2R,3S)-1,2-epoxy-3-N-(tert-butoxycarbonyl)amino-4-phenylbutane.

The above threo-1,2-epoxy-3-amino-4-phenylbutane derivatives (1) are intermediates for the production of HIV protease inhibitors which need to be ingested in high doses, and, therefore, it is of particular significance to develop a practical method for mass production of said derivatives.

SUMMARY OF THE INVENTION

In view of the above state of the art, it is an object of the present invention to provide a production method of high quality threo-1,2-epoxy-3-amino-4-phenylbutane derivatives (1) on a commercial scale in a simple, easy and efficient manner and with very high productivity. Another object of the invention is to develop a method of crystallizing the above derivatives in a high density state.

The present invention thus provides a production method of a threo-1,2-epoxy-3-amino-4-phenylbutane derivative of the above general formula (1)

which comprises treating, with a base, a threo-1-halo-2-hydroxy-3-amino-4-phenylbutane derivative of the following general formula (2):

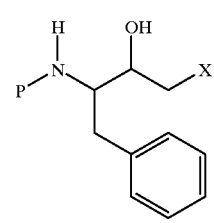

(2)

wherein P is as defined above, X represents a halogen atom and the configurations at positions 2 and 3 are (2S,3R) when they are (2S,3R) in the formula (1) or (2R,3S) when they are (2R,3S) in the formula (1), in a polar organic solvent or a solvent composed of a polar organic solvent and water, and adding the resulting reaction mixture to water to thereby cause the threo-1,2-epoxy-3-amino-4-phenylbutane derivative (1) to crystallize out.

The present invention further relates to a synthesis method of a threo-1,2-epoxy-3-amino-4-phenylbutane derivative (1)

which comprises treating, with a base, a threo-1-halo-2-hydroxy-3-amino-4-phenylbutane derivative (2) in a polar organic solvent or a solvent composed of a polar organic solvent and water.

The present invention further relates to a purification/isolation method of a threo-1,2-epoxy-3-amino-4-phenylbutane derivative (1) which comprises adding, to water, a solution of the threo-1,2-epoxy-3-amino-4-phenylbutane derivative (1) in a polar organic solvent or a solution of the threo-1,2-epoxy-3-amino-4-phenylbutane derivative (1) in a solvent composed of a polar organic solvent and water to thereby cause the threo-1,2-epoxy-3-amino-4-phenylbutane derivative (1) to crystallize out.

In the following, the present invention is described in detail.

DETAILED DISCLOSURE OF THE INVENTION

The threo-1,2-epoxy-3-amino-4-phenylbutane derivative (1), which is the desired compound to be produced by the method of the present invention, is a protected form of threo-1,2-epoxy-3-amino-4-phenylbutane having the amino group protected by a urethane type protective group.

In the above general formula (1), the group P attached to the amino group is an amino-protecting group. This amino-protecting group is a group capable of protecting an amino group and includes various routine protective groups such as those described in the relevant monographs or literature available in the art, for example "Protective Groups in Organic Synthesis", 2nd edition, John Wiley & Sons, 1991. As the protective group P in the above general formula (1), preferred is a urethane type protective group (also referred to as carbamate type protective group). Preferred as such group are, among others, aralkyloxycarbonyl groups and lower alkoxycarbonyl groups (the alkyl moiety having 1 to 6 carbon atoms, preferably 1 to 4 carbon atoms). More preferred are benzyloxycarbonyl, methoxycarbonyl, ethoxycarbonyl and tert-butoxycarbonyl. Particularly preferred is tert-butoxycarbonyl.

The configurations at positions 2 and 3 of the above threo-1,2-epoxy-3-amino-4-phenylbutane derivative (1) are either (2S,3R) or (2R,3S).

The threo-1-halo-2-hydroxy-3-amino-4-phenylbutane derivative of the above general formula (2), which serves as the substrate in the reaction involved in the production method according to the present invention, has the same configuration as the above threo-1,2-epoxy-3-amino-4-phenylbutane derivative (1). Thus, when the above threo-1,2-epoxy-3-amino-4-phenylbutane derivative (1), which is to be obtained, has the (2S,3R) configuration, the above threo-1-halo-2-hydroxy-3-amino-4-phenylbutane derivative (2) should have the (2S,3R) configuration. For obtaining the (2R,3S) product, the substrate should be of (2R,3S) configuration.

In the above general formula (2), the group P attached to the amino group is as mentioned above. X represents a halogen atom, such as a chlorine, bromine, fluorine or iodine atom. A chlorine or bromine atom is preferred and a chlorine atom is more preferred because of ease of substrate synthesis.

The above threo-1-halo-2-hydroxy-3-amino-4-phenylbutane derivative (2) can be prepared, for example, by reducing a 1-halo-2-oxo-3-amino-4-phenylbutane derivative of the following general formula (3):

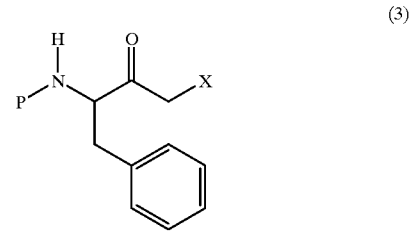

wherein P and X are as defined above and the configuration at position 3 is R when the threo-1-halo-2-hydroxy-3-amino-4-phenylbutane derivative (2) is intended to have the (2S, 3R) configuration, or S when the derivative (2) is intended to have the (2R,3S) configuration. More specifically, the (2R,3S) form of a threo-1-halo-2-hydroxy-3-amino-4-phenylbutane derivative (2) can be obtained by microbiological reduction of the corresponding (S) form 1-halo-2-oxo-3-amino-4-phenylbutane derivative (3), as described in Japanese Kokai Publication Hei-09-285.

The above 1-halo-2-oxo-3-amino-4-phenylbutane derivative (3) can be prepared by the methods described in Japanese Kokai Publication Sho-62-126158 and Japanese Kokai Publication Hei-02-42048, among others.

In cases where the above threo-1-halo-2-hydroxy-3-amino-4-phenylbutane derivative (2) is derived from the above 1-halo-2-oxo-3-amino-4-phenylbutane derivative (3) by a reduction reaction, there is a tendency for the threo-1-halo-2-hydroxy-3-amino-4-phenylbutane derivative (2) to contain the 1-halo-2-oxo-3-amino-4-phenylbutane derivative (3) as an impurity. However, even such threo-1-halo-2-hydroxy-3-amino-4-phenylbutane derivative (2) can be properly used as the reaction substrate to give the corresponding threo-1,2-epoxy-3-amino-4-phenylbutane derivative (1) of high quality in high yield. In this respect, the production method according to the present invention is highly advantageous.

According to the production method of the present invention, the threo-1-halo-2-hydroxy-3-amino-4-phenylbutane derivative (2) is treated, in the first step, with a base in a polar organic solvent or a solvent composed of a polar organic solvent and water to give the threo-1,2-epoxy-3-amino-4-phenylbutane derivative (1).

The above-mentioned polar organic solvent is not particularly restricted but includes, among others, aprotic polar organic solvents such as acetone, methyl ethyl ketone, tetrahydrofuran, 1,4-dioxane, 1,3-dioxolane, 1,2-dimethoxyethane, diethylene glycol dimethyl ether, triethylene glycol dimethyl ether, tetraethylene glycol dimethyl ether, polyethylene glycol dimethyl ether, 1,2-diethoxyethane, diethylene glycol diethyl ether, triethylene glycol diethyl ether, tetraethylene glycol diethyl ether, polyethylene glycol diethyl ether, acetonitrile, dimethylformamide and dimethyl sulfoxide; protic polar organic solvents such as alcohols, for example methanol, ethanol, n-propanol, isopropanol, n-butanol, sec-butanol, isobutanol and tert-butanol. These may be used singly, or two or more of them may be used in combination. The solvent may contain any other type of organic solvent if it will not produce any adverse effect.

When an alcohol is used as the above polar organic solvent, there is a tendency toward impurity formation. Therefore, in the treatment with a base, an aprotic polar organic solvent is preferably used. Ketones, such as acetone, ethers, such as tetrahydrofuran, acetonitrile and the like are preferred among others. Acetone is most preferred because of ease of handling and inexpensiveness, however.

In cases where a solvent composed of a polar organic solvent and water is used, the polar organic solvent is preferably selected from among organic solvents having relatively high affinity with water, more preferably from among organic solvents having highly affinity with water, still more preferably from among organic solvents fully miscible with water. The term "organic solvent fully miscible with water" generally means an organic solvent such that, when it is stirred gently with the same volume of pure water at a temperature of 20° C. and under atmospheric pressure, the resulting mixture, after flows have subsided, has a homogeneous appearance.

The solvent composed of a polar organic solvent and water preferably has a low water content from the standpoint of increasing the reaction rate but, from the standpoint of the ease of crystallization of the threo-1,2-epoxy-3-amino-4-phenylbutane derivative (1) after the reaction, a lower polar organic solvent content is preferred. The water/polar organic solvent ratio may vary according to such factors as the polar organic solvent species, strength of the base, and reaction temperature and therefore cannot be specified in general terms. The ratio, however, can be selected by carrying out a simple experiment. Generally, the ratio is not more than 10 by volume, preferably not more than 5, more preferably not more than 2.

The substrate concentration in the reaction mixture is not particularly restricted but, generally, the ratio of the threo-1-halo-2-hydroxy-3-amino-4-phenylbutane derivative (2) to the reaction solvent is not less than 5 w/v %, preferably not less than 10 w/v %.

The base to be used in the production method according to the invention is not particularly restricted but includes, among others, alkali metal hydroxides, alkali metal carbonates, alkaline earth metal hydroxides and alkaline metal carbonates. These may be used singly or two or more of them may be used combinedly. From the reaction rate viewpoint, alkali metal hydroxides and alkaline earth hydroxides are preferred and, from the viewpoint of inexpensiveness, ease of handling and/or ease of waste water treatment, for instance, alkali metal hydroxides such as lithium hydroxide, sodium hydroxide and potassium hydroxide are preferred. Among them, sodium hydroxide is particularly preferred.

The above base may be used in the solid form or in the form of an aqueous solution or suspension. From the operability viewpoint, however, it is preferably used as an aqueous solution. For example, a 1 to 20 N aqueous solution of an alkali metal hydroxide is favorably used.

The above base is used approximately in a stoichiometric amount or larger. The use of an excessively large amount is uneconomical. Generally, the base can be used in an amount of about 1 to 10 equivalents, preferably about 1 to 3 equivalents.

The reaction temperature in the step of treatment with a base is not particularly restricted. Thus, the reaction can be carried out at a temperature at which the reaction mixture will not solidify through at a temperature not higher than 50° C., preferably at a temperature not higher than about 30° C.

The reaction time for said step of treatment with a base is not particularly restricted. When the base is used in the above-mentioned amount and the reaction temperature is within the above range, it is possible to carry the reaction to complete generally in several minutes to 30 hours. When the base is used in an amount of about 1 to 3 equivalents and the reaction temperature is about 10° C. to about 30° C., the reaction can be carried to complete generally within several hours.

The second step in the production method according to the present invention is carried out by adding, to water, the reaction mixture obtained in the above manner to thereby cause the threo-1,2-epoxy-3-amino-4-phenylbutane derivative (1) to crystallize out.

In this crystallization step, the presence of water as a poor solvent is essential for properly reducing the solubility of the threo-1,2-epoxy-3-amino-4-phenylbutane derivative (1). However, the threo-1,2-epoxy-3-amino-4-phenylbutane derivative (1) tends to separate out as an oil (oily substance) in the presence of water. For example, when water is continuously added to the reaction mixture obtained, the threo-1,2-epoxy-3-amino-4-phenylbutane derivative (1) separates out as an oil (oily substance) and this oil (oily substance) solidifies and adheres to the crystallizer wall and/or stirrer in substantial amounts, resulting in deposition of tight scales and/or formation of hardly disintegrable lumps. As a result, unfavorable phenomena occur; for example, the crystallizer contents cannot be recovered neatly from the crystallizer. Therefore, the method of adding the reaction mixture to water is required so that nucleation may be promoted in highly water-rich state while such oil formation is prevented.

For successful crystallization, the reaction mixture obtained is added to water preferably over a period of half an hour or longer, more preferably over about 1 hour or longer, more preferably gradually over a still more extended period of time. Although there is no particular upper limit to the period of addition, the period of addition is generally not longer than about a day, preferably not longer than about half a day.

A procedure for maturation may be incorporated by interrupting the addition of the reaction mixture to water during the addition. This procedure is helpful in causing the crystallization to proceed while appropriately solidifying the oil (oily substance) accumulated with the addition of the reaction mixture to water. Although the timing of interposition of said maturation procedure is not particularly restricted, it is particularly effective to interpose the above maturation procedure at an early stage of addition, for example after addition of 1/1,000 to 1/10, preferably 1/1,00 to 1/20, of the reaction mixture obtained. The duration of such maturation treatment is preferably at least half an hour, more preferably about 1 hour or longer. After completion of the above maturation procedure, the addition of the reaction mixture obtained can of course be resumed for continued crystallization. If necessary, the procedures for addition and maturation may be repeated alternately.

By following the above procedure, it is possible to obtain a good crystal-containing slurry while suppressing the above-mentioned phenomenon inducedby solidification of the oil (oily substance).

The temperature for the crystallization step may depend on the species of threo-1,2-epoxy-3-amino-4-phenylbutane derivative (1), the polar organic solvent which coexists, the ratio between water and the polar organic solvent and other factors. For suppression of oil formation and promotion of crystallization, however, a low temperature is desirable. Generally, the crystallization is carried out preferably at a temperature at which the liquid will not solidify through at a temperature not higher than 40° C., more preferably not higher than about 30° C., still more preferably not higher than about 20 C., most preferably not higher than about 10° C. For improving the crystal characteristics, quality and yield, it is also possible, if necessary, to conduct heating and/or cooling after crystallization.

The ratio between water and the polar organic solvent in the crystallization solution is preferably selected so that the crystallization solution will not separate into two or more phases but the crystallization may proceed in a solution forming a homogeneous phase between water and the polar organic solvent. Such ratio cannot be specified in general terms since it depends on the species of threo-1,2-epoxy-3-amino-4-phenylbutane derivative (1), the polar organic solvent used, the crystallization temperature and the intended extent of impurity removal and other factors. However, the ratio can be easily selected by carrying out a simple experiment. When the polar organic solvent used has a high affinity for the threo-1,2-epoxy-3-amino-4-phenylbutane derivative (1), for instance, it is desirable to increase the proportion of water.

Generally, from the viewpoint of satisfactory crystallization and improved percent recovery of the threo-1,2-eopxy-3-amino-4-phenylbutane derivative (1), a high proportion of water is preferred. The weight ratio of the polar organic solvent/water in the crystallization sytem is thus preferably not more than 1, more preferably not more than about ½, still more preferably not more than about ¼. If necessary, for the purpose of promoting the crystallization and improving the recovery rate, the proportion of the polar organic solvent can be reduced by distilling off the polar organic solvent out of the system under reduced pressure, for instance, during and/or after the crystallization step.

The concentration of the threo-1,2-eopxy-3-amino-4-phenylbutane derivative (1) in the crystallization mixture is not particularly restricted but the crystallization can be carried out at a concentration of not lower than about 5% by weight.

As regards the intensity of stirring or degree of agitation in the step of crystallization, excessively weak stirring tends to result in insufficient dispersion, while excessively vigorous stirring results in formation of too fine crystals, hence formation of a frothy slurry. For obtaining crystals having satisfactory properties and uniform particle size, therefore, moderate stirring or moderate agitation is preferred.

In the crystallization step, the crystallization solution may contain some organic solvent other than the solvent derived from the above-mentioned reaction step, and/or an inorganic salt such as sodium chloride, each in a concentration at which no adverse effect is produced.

The above technology will be described in further detail, referring to a specific procedure.

In carrying out the crystallization, the base which may remain in the reaction mixture can be removed after completion of the reaction or in the crystallization step. A typical procedure for removing the base comprises neutralization with an acid. The acid to be used for neutralization is not particularly restricted but may be a mineral acid such as hydrochloric acid, sulfuric acid and phosphoric acid, an organic acid such as acetic acid and formic acid, and a salt thereof. Such acids may be used singly or in combination. Among such acids, mineral acids such as hydrochloric acid and sulfuric acid are preferred because of low cost, ease of handling and ease of waste water treatment, among others. A preferred combination of such an acid with the base in the practice of the present invention is a combination such that, upon neutralization, they form an inorganic salt facilitating waste water treatment.

An alternative method for removal of the base, which applies when the reaction mixture separates into two phases (an organic phase and an aqueous phase), comprises removing the aqueous phase containing a large amount of the base out of the system.

Another procedure for removing the base, which applies when the base has precipitated out from the reaction mixture, comprises filtering off the base.

For preventing the basic component and inorganic salt from contaminating the crystals as completely as possible, the reaction mixture after the removal of the base component by the above-mentioned procedure should be submitted to crystallization and the base still remaining in the crystallization solution be neutralized. The target degree of neutralization is such that the pH in the crystallization step will be 6 to 11, preferably 7 to 9. For preventing contamination of the crystals with the base component and inorganic salt, it is also effective to thoroughly wash the wet crystal crop with water.

For promoting crystallization (nucleation), it is preferred that seed crystals are added in carrying out the crystallization. The addition amount of seed crystals depends on the rate of addition of the reaction mixture obtained and other factors, hence cannot be specified in general terms. The preferred amount is at least 1% by weight relative to the threo-1,2-epoxy-3-amino-4-phenylbutane derivative (1) subjected to crystallization.

The thus-obtained crystals of the threo-1,2-epoxy-3-amino-4-phenylbutane derivative (1) can be recovered by an ordinary solid-liquid separation technique such as pressure filtration, filtration under reduced pressure or centrifugation and, after washing the wet cake with water containing a small amount of an organic solvent and/or with water, if necessary, they can be dried by drying under atmospheric pressure, fluidized-bed drying or vacuum drying, for instance.

According to the production method of the present invention, it is possible to produce a high-quality threo-1,2-epoxy-3-amino-4-phenylbutane derivative (1) very efficiently in a simple and easy manner. Generally, the yield based on the corresponding threo-1-halo-2-hydroxy-3-amino-4-phenylbutane derivative (2) can be expected to be not less than about 90 mole percent. The crystals of said compound as obtained can be expected to have a higher density as compared with the crystals obtained by the prior art methods, for example a bulk density upon loose packing of not less than 0.3 g/ml, preferably not less than 0.4 g/ml.

The method of synthesizing a threo-1,2-epoxy-3-amino-4-phenylbutane derivative (1) according to the second aspect of the present invention comprises the first step of the above-mentioned production method. Thus, it comprises treating a threo-1-halo-2-hydroxy-3-amino-4-phenylbutane derivative (2) with a base in a polar organic solvent or a solvent composed of a polar organic solvent and water. This method of synthesis can be carried out in the same manner as the first step of the above-mentioned method of production. Such method of synthesis can be expected to give the threo-1,2-epoxy-3-amino-4-phenylbutane derivative (1) in a reaction yield of not less than about 90 mole percent, preferably not less than about 95 mole percent.

The purification/isolation method according to the third aspect of the present invention comprises crystallizing a threo-1,2-epoxy-3-amino-4-phenylbutane derivative (1) by adding, to water, a solution of the threo-1,2-epoxy-3-amino-4-phenylbutane derivative (1) in a polar organic solvent or a solution of the threo-1,2-epoxy-3-amino-4-phenylbutane derivative (1) in a solvent composed of a polar organic solvent and water. By utilizing this purification/isolation method, it is possible to purify and isolate a threo-1,2-epoxy-3-amino-4-phenylbutane derivative (1) obtained by some reaction step other than the first step of the above-mentioned production method by following the same procedure as in the second step of the above-mentioned production method.

The reaction mixture obtained after reaction can of course be used as the solution of the threo-1,2-epoxy-3-amino-4- phenylbutane derivative (1) in a polar organic solvent or the solution of the threo-1,2-epoxy-3-amino-4-phenylbutane derivative (1) in a solvent composed of a polar organic solvent and water. The solution to be used may also be a solution separately prepared by dissolving a threo-1,2-epoxy-3-amino-4-phenylbutane derivative (1) in a polar organic solvent or a solvent composed of a polar organic solvent and water.

Further, it may be a modification of the reaction mixture obtained in the above manner as rendered more suited for crystallization by concentration or solvent substitution.

The polar organic solvent to be used in the above case is not particularly restricted but includes, among others, aprotic polar organic solvents such as acetone, methyl ethyl ketone, tetrahydrofuran, 1,4-dioxane, 1,3-dioxolane, 1,2-dimethoxyethane, diethylene glycol dimethyl ether, triethylene glycol dimethyl ether, tetraethylene glycol dimethyl ether, polyethylene glycol dimethyl ether, 1,2-diethoxyethane, diethylene glycol diethyl ether, triethylene glycol diethyl ether, tetraethylene glycol diethyl ether, polyethylene glycol diethyl ether, acetonitrile, dimethylformamide and dimethyl sulfoxide; protic polar organic solvents such as alcohols containing 1 to 4 carbon atoms, for example methanol, ethanol, n-propanol, isopropanol, n-butanol, sec-butanol, isobutanol and tert-butanol, and acetic acid. These may be used singly, or two or more of them may be used in combination.

Generally preferred as the above polar organic solvent is an organic solvent relatively high in affinity with water, more preferably an organic solvent high in affinity with water, still more preferably an organic solvent fully miscible with water. The term "organic solvent fully miscible with water" generally means an organic solvent such that, when it is stirred gently with the same volume of pure water at a temperature of 20° C. and under atmospheric pressure, the resulting mixture, after flowing has subsided, has a homogeneous appearance. Specifically, ketones such as acetone, lower alcohols (alcohols containing 1 to 4 carbon atoms) such as methanol, and acetonitrile are preferred among others. From the viewpoint of ease of handling, inexpensiveness and oil formation-inhibiting effect, among others, acetone and methanol are particularly preferred. In the step of crystallization, the mixture may contain some other organic solvent and/or an inorganic salt such as sodium chloride each in a concentration at which no adverse effect is produced.

In this purification/isolation method, the conditions other than those just mentioned above are the same as those mentioned above referring to the second step of the above-mentioned production method.

In accordance with such purification/isolation method, the recovery percentage of the high-quality threo-1,2-epoxy-3-amino-4-phenylbutane derivative (1) can be expected to be not less than about 90 mole percent, preferably not less than about 95 mole percent. The density of the crystals of said compound can be expected to be higher as compared with the crystals obtained by the prior art methods, for example a bulk density upon loose packing of not less than 0.3 g/ml, preferably not less than 0.4 g/ml.

BEST MODES FOR CARRYING OUT THE INVENTION

Figure 1:
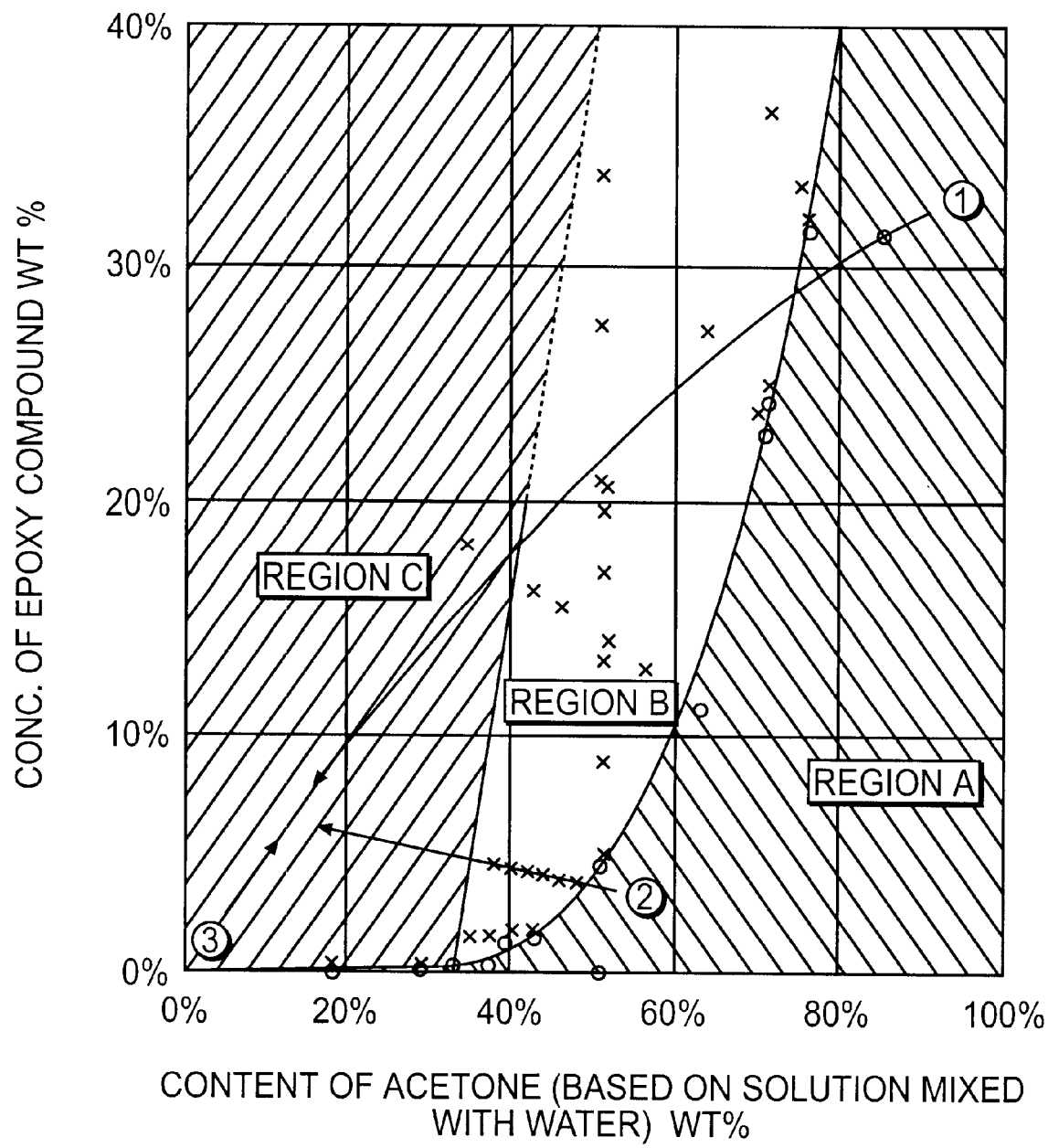
FIG. 1 is a diagram showing the change in phase separation state (at 5° C.) in a ternary system composed of (2R,3S)-1,2-epoxy-3-N-(tert-butoxycarbonyl)amino-4-phenylbutane [epoxy compound], acetone and water.

The following examples illustrate the present invention in further detail, They are, however, by no means limitative of the scope of the invention.

<Reference Experiment>

The three components (2R,3S)-1,2-epoxy-3-N-(tert-butoxycarbonyl)amino-4-phenylbutane [epoxy compound], acetone and water were blended in various arbitrarily selected proportions for examination of the phase separation states at 5° C. The results of this experiment are shown in FIG. 1. In the figure, the region A indicates a homogeneous liquid phase (epoxy compound dissolved; plotted by ○), the region B indicates a liquid-liquid two phase region (epoxy compound in the state of an oil, etc.; plotted by X), and the region C denotes a solid-liquid two phase region (epoxy compound crystallized; plotted by +).

From this diagram, it was revealed that the above ternary system covers three phase separation states according to the composition thereof. It is seen that by shifting the composition of a solution containing (2R,3S)-1,2-epoxy-3-N-(tert-butoxycarbonyl)amino-4-phenylbutane from the region A to the region C, it is possible to cause the (2R,3S)-1,2-epoxy-3-N-(tert-butoxycarbonyl)amino-4-phenylbutane to separate out but that it is difficult to inhibit the oily substance from solidifying by the technique comprising adding water to a solution containing (2R,3S)-1,2-epoxy-3-N-(tert-butoxycarbonyl)amino-4-phenylbutane (via the route indicated by an arrow 1) in the figure) or by the technique comprising distilling off acetone from a solution containing (2R,3S)-1,2-epoxy-3-N-(tert-butoxycarbonyl)amino-4-phenylbutane (via the route indicated by an arrow 2) in the figure) since, in both cases, the route of composition shifting passes through the region B where the liquid phase forms an oil (separates into two phases). On the contrary, it is seen that the technique comprising adding, to water, a solution containing (2R,3S)-1,2-epoxy-3-N-(tert-butoxycarbonyl)amino-4-phenylbutane (via the route indicated by an arrow 3) in the figure) can maintain the composition of the solution always in the region C where no oil formation occurs and therefore can cause favorable crystallization while avoiding oil formation.

EXAMPLE 1

In a nitrogen atmosphere, a 2-liter flask was charged in sequence with 250 g of water, 202 g of crystals of (2R,3S)-1-chloro-2-hydroxy-3-N-(tert-butoxycarbonyl)amino-4-phenylbutane [containing 200 g (0.667 mole) of pure substance and 2 g of (3S)-1-chloro-2-oxo-3-N-(tert-butoxycarbonyl)amino-4-phenylbutane as an impurity] and 400 g of acetone. While maintaining the temperature at 25° C., 133 g of a 30% (by weight) aqueous solution of sodium hydroxide was added dropwise over 2 hours with moderate stirring in a nitrogen atmosphere. After completion of the dropping, the stirring was continued for 1 hour and then discontinued, and the lower aqueous phase (pH 14) was separated. The upper acetone layer was passed through a filter and then 40 g of a 50% (by weight) aqueous solution of acetone was passed therethrough, to give 600 g of an acetone solution containing 175 g (0.665 mole) of (2R,3S)-1,2-epoxy-3-N-(tert-butoxycarbonyl)amino-4-phenylbutane (yield 100%). Water (2,300 g) was placed in a 5-liter flask and cooled to 5° C. While maintaining the temperature at 5° C., with moderate stirring in a nitrogen atmosphere, 2 g of seed crystals of (2R,3S)-1,2-epoxy-3-N-(tert-butoxycarbonyl)amino-4-phenylbutane were added to the flask and then the above acetone solution (600 g) cooled to 5° C. and containing (2R,3S)-1,2-epoxy-3-N-(tert-butoxycarbonyl) amino-4-phenylbutane was added dropwise over 4 hours. After completion of the dropping, the stirring was continued for 1 hour and then the resulting crystals were collected by filtration, washed with two 250 g portions of a cooled 10% (by weight) aqueous solution of acetone and with one 500 g portion of water at 25° C. and then thoroughly drained. The thus-obtained wet crystals were subjected to vacuum drying (1 to 4 mm Hg) at 25° to 30° C. until the water content and acetone content each was reduced to not more than 0.1% by weight, to give 166 g (0.630 mole) of (2R,3S)-1,2-epoxy-3-N-(tert-butoxycarbonyl)amino-4-phenylbutane (yield 93%, crystal purity 99.8%, bulk density upon loose packing 0.4 g/ml).

Comparative Example 1

The acetone solution containing (2R,3S)-1,2-epoxy-3-N-(tert-butoxycarbonyl)amino-4-phenylbutane as obtained in the same manner as in Example 1 was placed in a 5-liter flask and cooled to 5° C. While maintaining the temperature at 5° C., the addition of 2,300 g of water was started with moderate stirring in a nitrogen atmosphere. With the progress of the dropping, the mixture separated into two layers and the lower layer solidified and became lumpy, the stirring was stopped.

Comparative Example 2

To 200 g of crystals of (2R,3S)-1,2-epoxy-3-N-(tert-butoxycarbonyl)amino-4-phenylbutane as obtained in the same manner as in Example 1 was added 200 g of n-hexane and, after dissolution at 40° C., the solution was passed through a filter to give 400 g of a solution of (2R,3S)-1,2-epoxy-3-N-(tert-butoxycarbonyl)amino-4-phenylbutane in n-hexane. This n-hexane solution was placed in a one-liter flask and cooled to 5° C. over 4 hours with moderate stirring. After completion of the cooling, the stirring was continued for an hour and then crystals were filtered off, washed with one 200 g portion of cooled n-hexane and thoroughly drained. The thus-obtained wet crystals were subjected to vacuum drying (1 to 4 mm Hg) at 25° to 30° C. until a n-hexane content of not more than 0.1% by weight to give 145 g (0.550 mole) of crystals of (2R,3S)-1,2-epoxy-3-N-(tert-butoxycarbonyl)amino-4-phenylbutane (yield 73%, crystal purity 99.9%, bulk density upon loose packing 0.1 g/ml).

EXAMPLE 2

Water (75 g) was placed in a 200-ml flask and cooled to 5° C. Then, 25 g of an acetone solution containing 10 g of (2R,3S)-1,2-epoxy-3-N-(tert-butoxycarbonyl)amino-4-phenylbutane was added dropwise while moderately stirring at 600 rpm using an egg-shaped magnetic stirrer (3 cm). The dropping was conducted slowly until the amount dropped arrives at one third of the whole amount. Thereafter, the rate of dropping was gradually increased. The whole amount was thus dropped over 3 hours, to give a slurry. Crystals were filtered off and subjected to vacuum drying (1 to 4 mm Hg, 1 day) to give 9 g of (2R,3S)-1,2-epoxy-3-N-(tert-butoxycarbonyl)amino-4-phenylbutane.

Comparative Example 3

An acetone solution (25 g) containing 10 g of (2R,3S)-1,2-epoxy-3-N-(tert-butoxycarbonyl)amino-4-phenylbutane was placed in a 200-ml flask and cooled to 5° C. Then, 75 g of water was added dropwise with stirring at 600 rpm using an egg-shaped magnetic stirrer (3 cm). The mixture separated into two layers and the lower layer solidified and became lumpy, as a result, the stirring was stopped.

EXAMPLE 3

From a mixture composed of 10 g of (2R,3S)-1,2-epoxy-3-N-(tert-butoxycarbonyl)amino-4-phenylbutane, 2 g of sodium chloride, 16 g of acetone and 6 g of water was separated the acetone phase. Water (73 g) was placed in a 200-ml flask and cooled to 5° C. and then moderately stirred at 600 rpm using an egg-shaped magnetic stirrer (3 cm). Then, an amount specified in Table 1 of seed crystals were added, and the above acetone layer was added dropwise over a period specified in Table 1, to give a slurry. Crystals were filtered off and subjected to vacuum drying (1 to 4 mm Hg, 1 day) and then examined for weight percentage of particles passing through a standard sieve (14 mesh screen(1,190 μm)). The results thus obtained are shown in Table 1.

TABLE 1

| Amount of seed crystal | Period of dropping | Weight percentage of particles passing through a 14 mesh screen |
| --- | --- | --- |
| 0.5 g (5%) | 20 min | 98% |
| 0.1 g (1%) | 120 min | 100% |
| No addition (0%) | 120 min | 90% |

EXAMPLE 4

Water (50 g) was placed in a 200-ml flask (paddle type stirring blade, 5 cm) and cooled to 5° C. and then 50 g of a methanol solution containing 10 g of (2R,3S)-1,2-epoxy-3-N-(tert-butoxycarbonyl)amino-4-phenylbutane was added dropwise over 3 hours with stirring at 250 rpm, to give a slurry. Crystals were filtered off and subjected to vacuum drying (1 to 4 mm Hg, 1 day) to give 9 g of (2R,3S)-1,2-epoxy-3-N-(tert-butoxycarbonyl)amino-4-phenylbutane.

EXAMPLE 5

Water (50 g) was placed in a 200-ml flask (paddle type stirring blade, 5 cm) and cooled to 5° C. and then 19 g of an acetonitrile solution containing 10 g of (2R,3S)-1,2-epoxy-3-N-(tert-butoxycarbonyl)amino-4-phenylbutane was added dropwise over 3 hours with stirring at 250 rpm, to give a slurry. Crystals were filtered off and subjected to vacuum drying (1 to 4 mm Hg, 1 day) to give 9 g of (2R,3S)-1,2-epoxy-3-N-(tert-butoxycarbonyl)amino-4-phenylbutane.

EXAMPLE 6

An acetone solution (600 g) containing 175 g (0.665 mole) of (2R,3S)-1,2-epoxy-3-N-(tert-butoxycarbonyl)amino-4-phenylbutane obtained in the same manner as in Example 1 was cooled to 5° C. Water (2,300 g) was placed in a 5-liter flask and cooled to 5° C. While maintaining the temperature at 5° C., 2 g of seed crystals of (2R,3S)-1,2-epoxy-3-N-(tert-butoxycarbonyl)amino-4-phenylbutane were added with moderate stirring in a nitrogen atmosphere. Then, 12 g of the above acetone solution cooled to 5° C. and containing (2R,3S)-1,2-epoxy-3-N-(tert-butoxycarbonyl) amino-4-phenylbutane was added dropwise over 5 minutes. After completion of the dropping, the stirring was continued for 1 hour and, thereafter, the remaining portion of the acetone solution containing (2R,3S)-1,2-epoxy-3-N-(tert-butoxycarbonyl)amino-4-phenylbutane was added dropwise over 4 hours. After completion of the dropping, the stirring was continued for 1 hour and then crystals were filtered off, washed with two 250 ml portions of a cooled 10% (by weight) aqueous solution of acetone and with one 500 g portion of water at 25° C. and thoroughly drained. The wet crystals obtained were subjected to vacuum drying (1 to 4 mm Hg) at 25° to 30° C. until a moisture content of not more than 0.1% by weight and an acetone content of not more than 0.1% by weight, to give 170 g (0.646 mole) of (2R,3S)-1, 2-epoxy-3-N-(tert-butoxycarbonyl)amino-4-phenylbutane (yield 97%, crystal purity 99.8%, bulk density upon loose packing 0.4 g/ml).

INDUSTRIAL APPLICABILITY

The present invention, which has the constitution mentioned hereinabove, makes it possible to produce high quality threo-1,2-epoxy-3-amino-4-phenylbutane derivatives in a simple and easy and efficient manner with a very high productivity on a commercial scale. It also makes it possible to obtain the above derivatives as crystals with a high density.

What is claimed is:

1. A production method of a threo-1,2-epoxy-3-amino-4-phenylbutane compound of the formula (1):

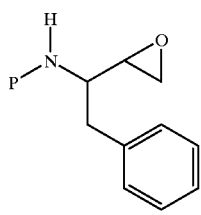

(1)

wherein P represents a urethane-type amino-protecting group and the configurations at 2 and 3 positions are (2S,3R) or (2R,3S), which comprises treating, with a base, a threo-1-halo-2-hydroxy-3-amino-4-phenylbutane compound of the formula (2):

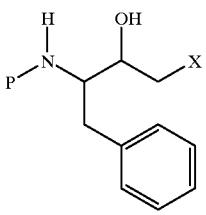

(2)

wherein P is as defined above, X represents a halogen atom and the configurations at positions 2 and 3 are (2S,3R) when they are (2S,3R) in formula (1) or (2R,3S) when they are (2R,3S) in the formula (1), in a polar organic solvent or a solvent composed of a polar organic solvent and water, and adding the resulting reaction mixture to water to thereby cause the threo-1,2-epoxy-3-amino-4-phenylbutane compound (1) to crystallize out.

2. The production method according to claim 1, wherein the polar organic solvent is an aprotic polar organic solvent.

3. The production method according to claim 2, wherein the aprotic polar organic solvent is acetone.

4. The production method according to claim 1, wherein the base is at least one member selected from the group consisting of alkali metal hydroxides, alkali metal carbonates, alkaline earth metal hydroxides and alkaline earth metal carbonates.

5. The production method according to claim 4, wherein the base is an alkaline metal hydroxide.

6. The production method according to claim 1, wherein the treatment with the base is carried out at a temperature not higher than 50° C.

7. The production method according to claim 1, wherein the addition of the resulting reaction mixture to water is carried out over a period of not shorter than half an hour.

8. The production method according to claim 1, wherein the addition of the resulting reaction mixture to water is interrupted during the addition to thereby incorporate a procedure for maturation.

9. The production method according to claim 8, wherein the period for the maturation procedure is not shorter than half an hour.

10. The production method according to claim 8, wherein the maturation procedure is incorporated at a time when 1/1,000 to 1/10 of the whole amount of the resulting reaction mixture has been added.

11. The production method according to claim 1, wherein the crystallization is effected at a temperature not higher than 40° C.

12. The production method according to claim 1, wherein the weight ratio of the polar organic solvent/water in the crystallization solution is not higher than 1.

13. The production method according to claim 1, wherein the base remaining in the system after treatment with the base is removed from the system prior to effecting the crystallization.

14. The production method according to claim 1, wherein a seed crystal is added in effecting the crystallization.

15. The production method according to claim 14, wherein an amount of the seed crystal to be added is at least 1% by weight relative to the threo-1,2-epoxy-3-amino-4-phenylbutane compound (1) to be subjected to crystallization.

16. The production method according to claim 1, wherein the threo-1-halo-2-hydroxy-3-amino-4-phenylbutane compound (2) is obtainable by subjecting a 1-halo-2-oxo-3-amino-4-phenylbutane compound of the formula (3) to a reduction reaction:

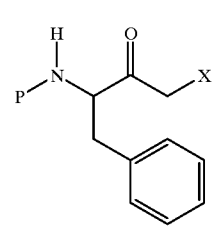

(3)

wherein P represents a urethane-type amino-protecting group, X represents a halogen atom and the configuration at position 3 is R when the threo-1-halo-2-hydroxy-3-amino-4-phenylbutane compound (2) is intended to have the (2S, 3R) configuration, or S when the compound (2) is intended to have the (2R,3S) configuration.

17. The production method according to claim 16, wherein the threo-1-halo-2-hydroxy-3-amino-4-phenylbutane compound (2) contains the 1-halo-2-oxo-3-amino-4-phenylbutane compound (3) as an impurity.

18. A synthesis method of a threo-1,2-epoxy-3-amino-4-phenylbutane compound of the formula (1):

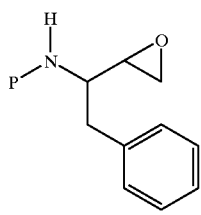

(1)

wherein P represents a urethane-type amino-protecting group and the configurations at 2 and 3 positions are (2S,3R) or (2R,3S), which comprises treating, with a base, a threo-1-halo-2-hydroxy-3-amino-4-phenylbutane compound of the formula (2):

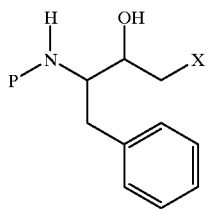

(2)

wherein P is as defined above, X represents a halogen atom and the configurations at positions 2 and 3 are (2S,3R) when they are (2S,3R) in the formula (1) or (2R,3S) when they are (2R,3S) in the formula (1), in an aprotic polar organic solvent or a solvent composed of an aprotic polar organic solvent and water.

19. The synthesis method according to claim 18, wherein the aprotic polar organic solvent is acetone.

20. The synthesis method according to claim 18, wherein the base is at least one member selected from the group consisting of alkali metal hydroxides, alkali metal carbonates, alkaline earth metal hydroxides and alkaline earth metal carbonates.

21. The synthesis method according to claim 20, wherein the base is an alkaline metal hydroxide.

22. The synthesis method according to claim 18, wherein the treatment with the base is carried out at a temperature not higher than 50° C.

23. The synthesis method according to claim 18, wherein the base remaining in the system after reaction is removed from the system.

24. The synthesis method according to claim 18, wherein the threo-1-halo-2-hydroxy-3-amino-4-phenylbutane compound (2) is obtainable by subjecting a 1-halo-2-oxo-3-amino-4-phenylbutane compound of the formula (3) to a reduction reaction:

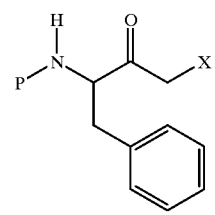

(3)

wherein P represents a urethane-type amino-protecting group, X represents a halogen atom and the configuration at position 3 is R when the threo-1-halo-2-hydroxy-3-amino-4-phenylbutane compound (2) is intended to have the (2S,3R) configuration, or S when the compound (2) is intended to have the (2R,3S) configuration.

25. The synthesis method according to claim 24, wherein the threo-1-halo-2-hydroxy-3-amino-4-phenylbutane compound (2) contains the 1-halo-2-oxo-3-amino-4-phenylbutane compound (3) as an impurity.

26. A purification/isolation method of a threo-1,2-epoxy-3-amino-4-phenylbutane compound of the formula (1):

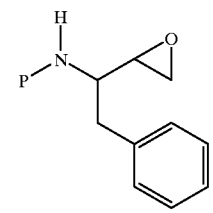

(1)

wherein P represents a urethane-type amino-protecting group and the configurations at 2 and 3 positions are (2S,3R) or (2R,3S), which comprises adding, to water, a solution of the threo-1,2-epoxy-3-amino-4-phenylbutane compound (1) in a polar organic solvent or a solution of the threo-1,2-epoxy-3-amino-4-phenylbutane compound (1) in a solvent composed of a polar organic solvent and water to thereby cause the threo-1,2-epoxy-3-amino-4-phenylbutane compound (1) to crystallize out.

27. The purification/isolation method according to claim 26, wherein the addition of the solution to water is carried out over a period of not shorter than half an hour.

28. The method according to claim 26, wherein the addition of the solution to water is interrupted during the addition to thereby incorporate a procedure for maturation.

29. The method according to claim 28, wherein the period for the maturation procedure is not shorter than half an hour.

30. The method according to claim 28, wherein the maturation procedure is incorporated at a time when 1/1,000 to 1/10 of the whole amount of the solution has been added.

31. The purification/isolation method according to claim 26, wherein the crystallization is effected at a temperature not higher than 40° C.

32. The purification/isolation method according to claim 26,
wherein the weight ratio of the polar organic solvent/water in the crystallization solution is not higher than 1.

33. The purification/isolation method according to claim 26,
wherein a seed crystal is added in effecting the crystallization.

34. The purification/isolation method according to claim 33,
wherein an amount of the seed crystal to be added is at least 1% by weight relative to the threo-1,2-epoxy-3-amino-4-phenylbutane compound (1) to be subjected to crystallization.

35. The purification/isolation method according to claim 26,
wherein the polar organic solvent is an aprotic polar organic solvent.

36. The purification/isolation method according to claim 35,
wherein the aprotic polar organic solvent is acetone.

37. The purification/isolation method according to claim 26,
wherein the polar organic solvent is a protic polar organic solvent.

38. The purification/isolation method according to claim 37,
wherein the protic polar organic solvent is an alcohol containing 1 to 4 carbon atoms.

39. The purification/isolation method according to claim 38,
wherein the alcohol containing 1 to 4 carbon atoms is methanol.

40. The method according to claim 1,
wherein the urethane type amino-protecting group represented by P in the formula (1), (2) and (3) is an aralkyloxycarbonyl group or a lower alkoxycarbonyl group.

41. The method according to claim 40,
wherein the urethane type amino-protecting group is benzyloxycarbonyl, methoxycarbonyl, ethoxycarbonyl or tert-butoxycarbonyl.

42. The method according to claim 41,
wherein the urethane type amino-protecting group is tert-butoxycarbonyl.

* * * * *